United States Patent [19]

Morton et al.

[11] Patent Number: 5,210,206
[45] Date of Patent: May 11, 1993

[54] 1,3-OXAZOLYL SUBSTITUTED BIPHENYL

[75] Inventors: Howard E. Morton, Gurnee; Biswanath De, Buffalo Grove; Daniel J. Kerkman, Lake Villa, all of Ill.

[73] Assignee: Abbott Laboratories, Abbott Park, Ill.

[21] Appl. No.: 819,537

[22] Filed: Jan. 10, 1992

Related U.S. Application Data

[63] Continuation-in-part of Ser. No. 744,241, Aug. 15, 1991, which is a continuation-in-part of Ser. No. 580,400, Sep. 10, 1990, abandoned.

[51] Int. Cl.$^5$ .......................................... C07D 263/10
[52] U.S. Cl. ..................................... 548/238; 548/237
[58] Field of Search ................................ 548/237, 238

[56] References Cited

FOREIGN PATENT DOCUMENTS 396014 11/1990 European Pat. Off. .
420237 4/1991 European Pat. Off. .

OTHER PUBLICATIONS

Drugs of the Future 16 305–309 (1991).

Primary Examiner—John M. Ford
Assistant Examiner—Y. N. Gupta
Attorney, Agent, or Firm—Steven R. Crowley

[57] ABSTRACT

The present invention relates to a process for the preparation of a compound of the formula:

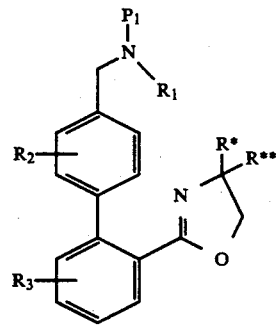

wherein $R_1$ is selected from the group consisting of hydrogen, loweralkyl, loweralkoxy-substituted loweralkyl, lower alkenyl, lower alkynyl, cycloalkyl and cycloalkylalkyl; $R_2$ is selected from the group consisting of hydrogen, loweralkyl, loweralkoxy-substituted loweralkyl, halogen and loweralkoxy; $R_3$ is selected from hydrogen, loweralkyl, and halogen; R* and R** are independently selected from loweralkyl and $P_1$ is hydrogen or an nitrogen-protecting group; or an acid addition salt thereof.

6 Claims, No Drawings

1,3-OXAZOLYL SUBSTITUTED BIPHENYL

This is a continuation-in-part of U.S. patent application Ser. No. 744,241, filed Aug. 15, 1991, which is a continuation-in-part of U.S. application Ser. No. 580,400, filed Sept. 10, 1990.

TECHNICAL FIELD

The present invention relates to a process for the preparation of a substituted biphenyl.

BACKGROUND OF THE INVENTION

Compounds which are angiotensin II antagonists are currently being investigated for treatment of various cardiovascular diseases, including the treatment of hypertension. Angiotensin II antagonists generally comprise a substituted biphenyl moiety which is linked to a heterocyclic moiety. Angiotensin II antagonists of particular interest are compounds of the formula 1:

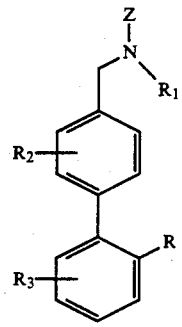

wherein R is 5-tetrazolyl or —COOR' wherein R' is hydrogen or loweralkyl, $R_1$ is hydrogen, loweralkyl, loweralkoxy-substituted loweralkyl, lower alkenyl, lower alkynyl, cycloalkyl or cycloalkylalkyl, $R_2$ is hydrogen, loweralkyl, loweralkoxy-substituted loweralkyl, halogen or loweralkoxy, $R_3$ is hydrogen, loweralkyl or halogen and Z is an nitrogen-containing heterocycle. Compounds of formula 1 are disclosed in U.S. patent application Ser. No. 744,241 which is incorporated herein by reference.

More preferred angiotensin II antagonists are compounds of formula 1 wherein R is 5-tetrazolyl.

Most preferred angiotensin II antagonists are compounds of formula 2:

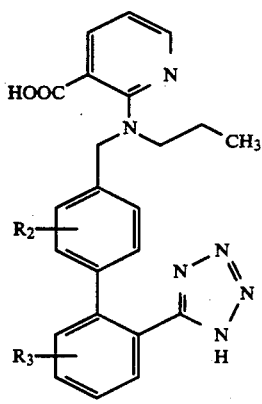

wherein $R_2$ is hydrogen, loweralkyl, loweralkoxy-substituted loweralkyl, halogen or loweralkoxy and $R_3$ is hydrogen, loweralkyl or halogen.

DISCLOSURE OF THE INVENTION

The present invention relates to an intermediate which is useful for the preparation of compounds of formula 1 and 2. The intermediate is a compound of formula 3:

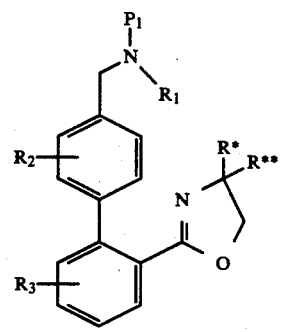

wherein $R_1$ is hydrogen, loweralkyl, loweralkoxy-substituted loweralkyl, lower alkenyl, lower alkynyl, cycloalkyl or cycloalkylalkyl, $R_2$ is hydrogen, loweralkyl, loweralkoxy-substituted loweralkyl, halogen or loweralkoxy, $R_3$ is hydrogen, loweralkyl or halogen, R* and R** are independently selected from loweralkyl and $P_1$ is hydrogen or an nitrogen-protecting group; or an acid addition salt thereof.

The present invention also relates to a process for the preparation of a compound of formula 3.

A process for the preparation of 3 is shown in Scheme 1. Substituted benzaldehyde 4 ($R_2$ is hydrogen, loweralkyl, loweralkoxy-substituted loweralkyl, halogen or loweralkoxy and X is Br or I) is reacted with an amine $R_1NH_2$ wherein $R_1$ is hydrogen, loweralkyl, loweralkoxy-substituted loweralkyl, lower alkenyl, lower alkynyl, cycloalkyl or cycloalkylalkyl (for example, n-propylamine, n-butylamine or cyclopropylmethylamine and the like) in a protic solvent (for example, methanol, ethanol or isopropanol and the like), followed by reduction of the resulting imine (for example, by catalytic hydrogenation using platinum on carbon or platinum oxide and the like or by reduction with sodium borohydride or sodium cyanoborohydride-acetic acid and the like) to give 5a. Alternatively, reaction of 4 with $R_1NH_2$ in an aprotic solvent (for example, in toluene or methylene chloride and the like with removal of water (for example, azeotropic removal or with molecular seives or magnesium sulfate and the like), followed by addition of a metal hydride reducing agent (for example, sodium cyanoborohydride in tetrahydrofuran, acetic acid or a mixture containing both, borane.dimethylamine in acetic acid or lithium aluminum hydride in ether or tetrahydrofuran and the like) gives the secondary amine 5a.

Protection of the amine nitrogen by reaction of 5a with an N-protecting reagent (for example, trityl chloride or tosyl chloride and the like) in an inert solvent (for example, methylene chloride, toluene, tetrahydrofuran, 1,2-dichloroethane or dimethylformamide and the like) in the presence of an amine base (for example, triethylamine, diisopropylethylamine or pyridine and the like) at a temperature of from about −20° C. to about 120° C. gives N-protected amine 5b ($P_1$ is an nitrogen-protecting group, for example, trityl or tosyl and the like). Protection of the amine nitrogen by reaction of 5a with an N-protecting reagent (for example, di-t-butyl-dicarbonate and the like) toluene/water and the like) in the presence of a base (for example, sodium bicarbonate or potassium carbonate and the like) at a temperature of from about −20° C. to about 120 ° C. gives N-protected amine 5b (P₁ is an nitrogen-protecting group, for example, t-butyloxycarbonyl and the like).

Grignard reagent 6 is prepared by reaction of 5b with magnesium turnings in an inert solvent (for example, tetrahydrofuran, diethyl ether/tetrahydrofuran mixtures or N,N,N',N'-tetramethylethylenediamine (TMEDA)/1,3-dimethyl-3,4,5,6-tetrahydro-2(1H)-pyrimidinone (DMPU) and the like) using an activating agent or process (for example, 1,2-dibromoethane, iodine, iodochloroethane or sonication and the like). Reaction of 6 with oxazoline 1 (R* and R** are independently selected from loweralkyl, R₃ is hydrogen, loweralkyl or halogen and Y is loweralkoxy or halogen, preferably, R* and R** are methyl and Y is methoxy) affords the biphenyl compound 3a. Nitrogen-deprotection (for example, using acetic acid in aqueous methanol or aqueous ethanol, hydrochloric acid in acetone, p-toluenesulfonic acid in acetone or oxalic acid in tetrahydrofuran/water and the like) at a temperatures of from ambient temperature to about the reflux temperature of the solvent affords the secondary amine 3b.

Alternatively, compound 5b can be reacted with an organolithium reagent (for example, n-butyl lithium or t-butyl lithium and the like) in an inert solvent (for example, tetrahydrofuran and the like) at a temperature of from about −78° C. to about room temperature to provide 6 wherein MgX is replaced by Li. This lithium derivative can then be reacted with 7 according to Scheme 1 to provide 3a.

Compound 3b can be further elaborated to an angiotensin II antagonist by reaction with the appropriate chlorinated nitrogen-containing heterocycle under concentrated conditions (for example, neat or at a concentration of 2 moles per liter or greater) in an inert solvent (for example, toluene, benzene, n-butanol, dimethylsulfoxide or dimethylformamide and the like) in the presence of a base such as triethylamine, Hunig's base (diisopropylethylamine), 1,8-diazabicyclo[5.4.0]undec-7-ene (DBU), 1,5-diazabicyclo[4.3.0]non−5-ene (DBN) or potassium carbonate and the like in the presence or absence of a catalytic amount of tetrabutyl ammonium bromide at a temperature of from about 50° C. to about the reflux temperature of the solvent to give 8. Reaction of 8 in pyridine with phosphorous oxychloride at a temperature of from about 50° C. to about 120° C. affords the nitrile 9. Reaction of the nitrile 9 with trimethyltin azide, hydrazoic acid, lithium chloride/sodium azide, sodium azide/aluminum chloride, trimethylsilylazide/dibutyltin oxide, trimethylsilylazide/dimethyltin oxide or sodium azide/ammonium chloride and the like in an inert solvent (for example, toluene, benzene, dimethylformamide or xylene and the like) at a temperature of from about 60° C. to about the reflux temperature of the solvent affords the tetrazole 10.

Alternatively, oxazoline 3b can be reacted with pyridine and POCl₃ at a temperature of from about 50° C. to about 120° C. to provide nitrile 9 (Z=H). Tetrazole formation, followed by reaction with the appropriate chlorinated nitrogen-containing heterocycle, provides 10.

Also, oxazoline 8 can be hydrolyzed (for example, aqueous hydrochloric acid or reaction with methyl iodide followed by basic hydrolysis (1N NaOH) and the like) to give the carboxylic acid 11. Compound 11 can be esterified, if desired.

In a preferred embodiment of the present invention (Scheme 2), 4-bromobenzaldehyde 12 is reacted with n-propylamine in methanol and then catalytically hydrogenated using a platinum on carbon catalyst to give 13a. The amine nitrogen is protected with a trityl group by reaction of 13a with tritylchloride and triethylamine in methylene chloride to give 13b. Grignard reagent 14 is prepared by reacting 13b with magnesium turnings and a catalytic amount of dibromoethane in tetrahydrofuran. Grignard reagent 14 is reacted with oxazoline 15 to give the biphenyl compound 16. The trityl group is removed using acetic acid in methanol to give the free amine 17. The amine is reacted with methyl 2-chloronicotinate in toluene containing triethylamine to give the tertiary amine 18. Treatment of 18 with phosphorous oxychloride in pyridine converts the oxazoline to the nitrile 19. Treatment of the nitrile with trimethyltin azide in toluene, followed by hydrogen chloride, affords the tetrazole 20. Sodium hydroxide hydrolysis converts the ester to the carboxylic acid 21.

SCHEME 1

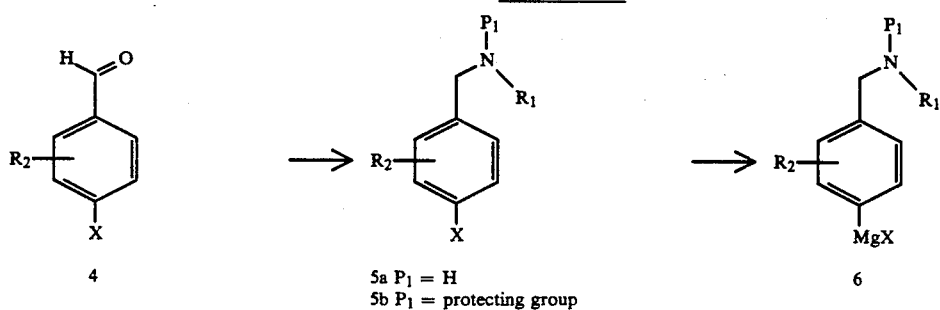

4

5a P₁ = H
5b P₁ = protecting group

6

-continued
SCHEME 1
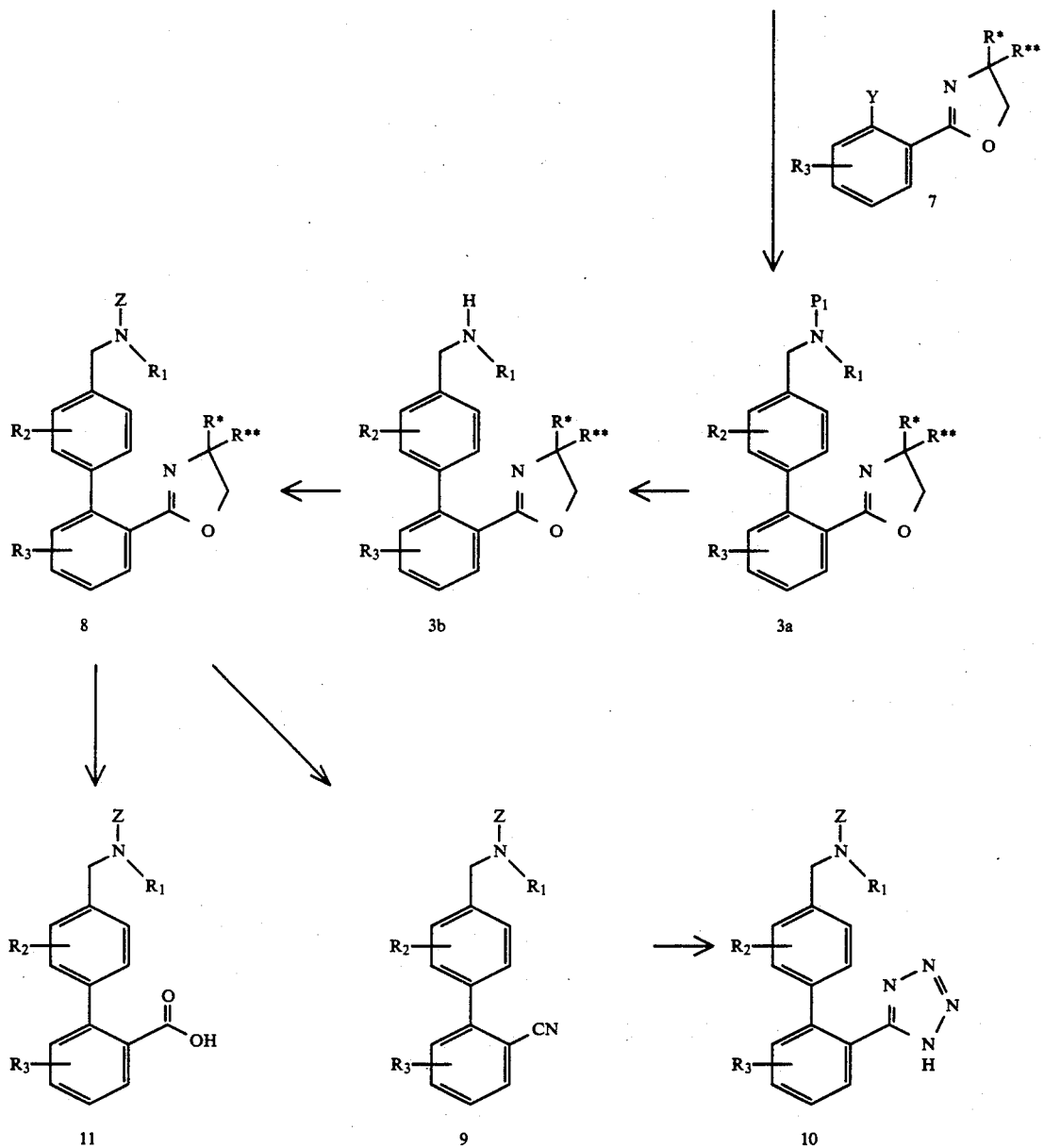
SCHEME 2
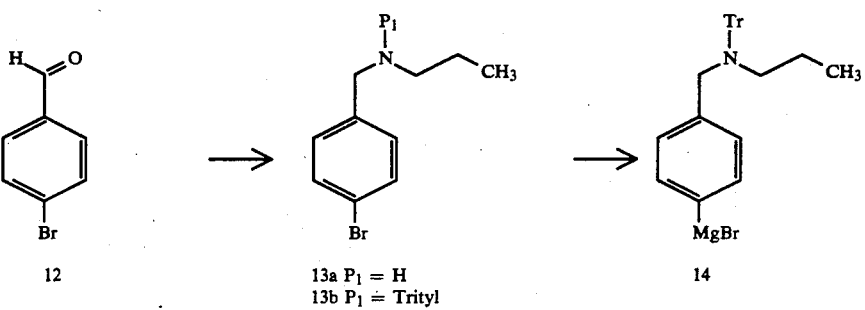

-continued
SCHEME 2

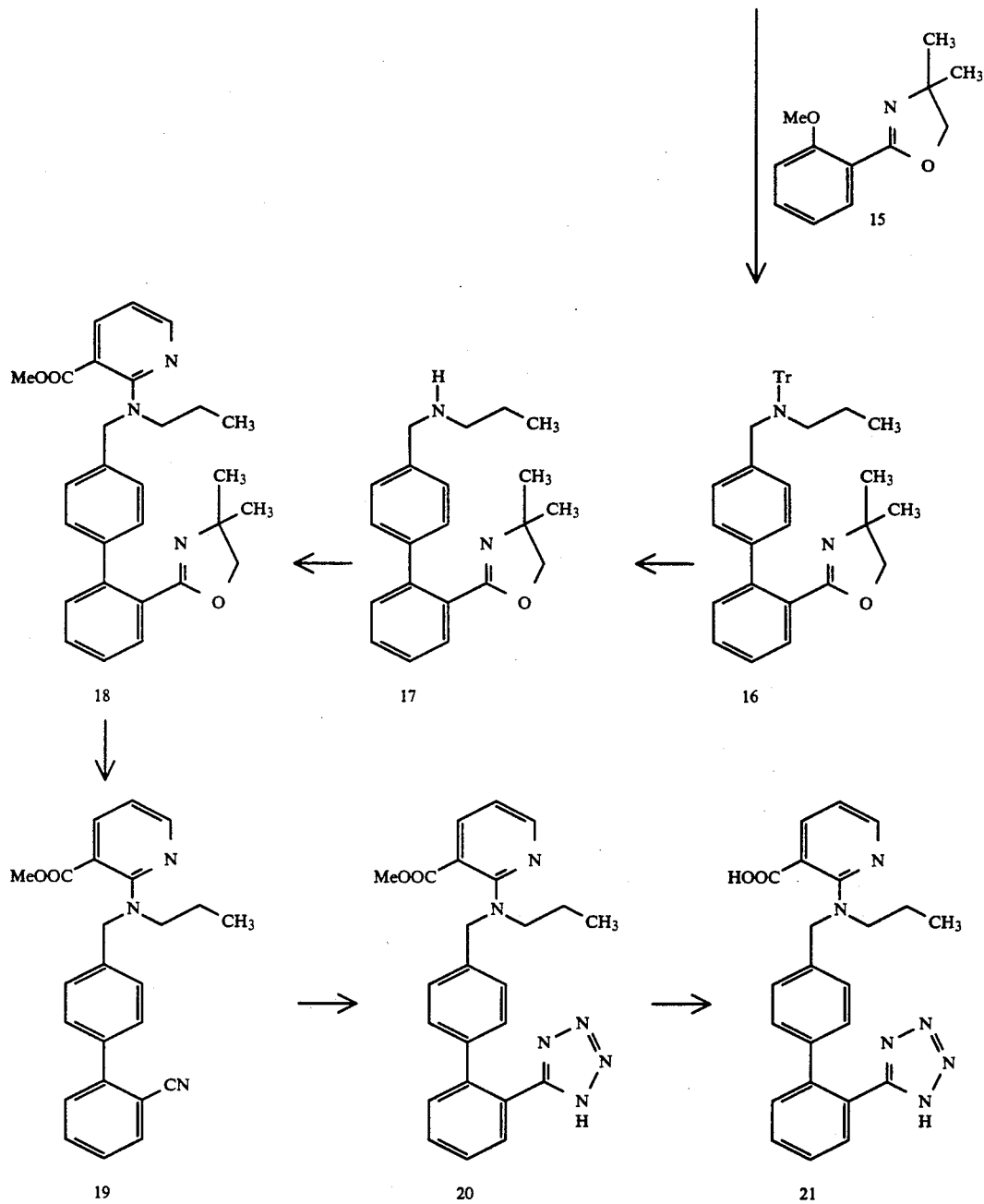

The term "loweralkyl" as used herein refers to a straight or branched chain alkyl radical having from 1 to 7 carbon atoms including, but not limited to, methyl, ethyl, n-propyl, iso-propyl, nbutyl, iso-butyl, sec-butyl, n-pentyl, 2-methylbutyl, 2,2-dimethylpropyl, n-hexyl, 2-methylpentyl, 2,2-dimethylbutyl, n-heptyl and the like.

The term "lower alkenyl" as used herein refers to a branched or straight chain having two to ten carbon atoms and which also has one or more carbon-carbon double bonds.

The term "lower alkynyl" as used herein refers to a branched or straight chain having two to ten carbon atoms and which also has one or more carbon-carbon triple bonds.

The term "loweralkoxy-substituted loweralkyl" as used herein refers to a loweralkyl radical to which is appended a loweralkoxy group.

The term "cycloalkyl" as used herein refers to an alicyclic ring having 3 to 7 carbon atoms including, but not limited to, cyclopropyl, cyclopentyl, cyclohexyl and the like.

The term "cycloalkylalkyl" as used herein refers to a cycloalkyl residue appended to a loweralkyl radical and includes, but is not limited to, cyclohexylmethyl, cyclopentylmethyl and the like.

The term "halo" or "halogen" as used herein refers to Cl, Br, F or I.

The term "alkoxy" or "loweralkoxy" as used herein refers to $R_{10}O$—wherein $R_{10}$ is a loweralkyl group.

The term "nitrogen-containing heterocycle" as used herein refers to an aromatic nitrogen containing heterocycle, for example, 3-methoxycarbonylpyrid-2-yl. Other nitrogen-containing heterocycles are disclosed and exemplified in U.S. patent application Ser. No. 744,241 which is incorporated herein by reference.

The term "N-protecting group", "nitrogen-protecting group" or "N-protected" as used herein refers to those groups intended to protect an amino group against undersirable reactions during synthetic procedures. Commonly used N-protecting groups are disclosed in Greene, "Protective Groups In Organic Synthesis," (John Wiley & Sons, New York (1981)), which is hereby incorporated by reference. N-protecting groups comprise carbamates, amides, N-alkyl derivatives, amino acetal derivatives, N-benzyl derivatives, imine derivatives, enamine derivatives and N-heteroatom derivatives. Preferred N-protecting groups are formyl, acetyl, benzoyl, pivaloyl, phenylsulfonyl, benzyl, benzyl wherein the phenyl ring is substituted with one, two or three alkoxy groups, triphenylmethyl (trityl), triphenylmethyl wherein one or more of the phenyl rings is substituted with a loweralkyl, halo or alkoxy group, t-butyloxycarbonyl (Boc), benzyloxycarbonyl (Cbz) and the like.

The term "acid addition salt" as used herein refers to salts derived from inorganic or organic acids. These salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptonate, glycerophosphate, hemisulfate, heptonate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, pamoate, pectinate, persulfate, phosphate, 3-phenylpropionate, picrate, pivalate, propionate, succinate, tartrate, thiocyanate, tosylate, and undecanoate.

Examples of acids which may be employed to form acid addition salts include such inorganic acids as hydrochloric acid, hydrobromic, sulphuric acid and phosphoric acid and such organic acids as oxalic acid, maleic acid, succinic acid, methanesulfonic acid and citric acid and the like.

The following examples will serve to further illustrate the process of the invention.

EXAMPLE 1

N-(4-Bromophenylmethyl)-N-propylamine

To 4-bromobenzaldehyde (100 g, 0.54 mol) and n-propylamine (36.3 g, 0.60 mol) in methanol (100 mL) was added 5% platinum on carbon (1.00 g). This mixture was shaken in a Parr hydrogenation reactor overnight to complete formation of the Schiff base. The reaction was then hydrogenated under 4 atmospheres of hydrogen until the theoretical uptake of hydrogen had been consumed. The catalyst was removed by filtration through a 0.45 μ nylon frit and washed with methanol. The filtrate was concentrated under reduced pressure and the residue obtained dissolved in ether (500 mL). The ether solution was washed with water (2×100 mL), 10% sodium bicarbonate solution (2×100 mL), and water (2×100 mL), dried over magnesium sulfate, filtered, and concentrated under reduced pressure to afford the crude title compound (121.34 g). GC-MS showed this material to be 98.5% pure product containing 1.5% of the desbromo compound; the yield is 96.93% based on the GC purity of the product obtained. A sample of material thus obtained was purified by bulb-to-bulb distillation (bath temperature 130°-150° C., 0.18 torr). $^1$H NMR (CDCl$_3$, 300 MHz) δ 0.92 (t, J=7.4 Hz, 3H), 1.36 (bs, 1H), 1.53 (tq, J$_1$=J$_2$=7.4 Hz, 2H), 2.57 (t, J=7.4Hz, 2H), 3.74 (s, 2H), 7.20 (d, J=9Hz, 2H), 7.44 (d, J=9Hz, 2H). IR (film) 1430, 1060 cm$^{-1}$. MS (DCI/NH$_3$) m/e 228, 230 (M+H)$^+$. Anal Calcd. for C$_{10}$H$_{14}$BrN: C, 52.64H, 6.18; N, 6.14. Found: C, 53.12; H, 6.24; N, 6.18.

EXAMPLE 2

N-(4-Bromophenylmethyl)-N-propylamine-N-tritylamine

To a stirred solution of the compound resulting from Example 1 (49.7 g, 0.218 mol) dissolved in methylene chloride (500 mL) under nitrogen at 0° C. was added triethylamine (36 mL), followed by tritylchloride (63.8 g, 0.229 mol). The reaction mixture was allowed to warm to ambient temperature and stirred for an additional 18 hours. The resultant slurry was diluted with methylene chloride (1 L) and washed with water (2×), 10% aqueous sodium bicarbonate, and brine. Drying over magnesium sulfate and concentrating under reduced pressure gave a pale yellow oil. Crystallization from ethanol (500 mL) afforded the title compound as a white solid (103 g, 83%). m.p. 136°-137° C. $^1$H NMR (CDCl$_3$, 300 MHz) δ 0.47 (bt, J=7.5Hz, 3H), 0.95 (m, 2H), 2.24 (m, 2H), 3.57 (s, 2H), 7.17 (bdd, J$_1$=J$_2$=7.5 Hz, 3H), 7.27 (dd, J=7.5Hz, 6H), 7.45 (s, 4H), 7.60 (d, J=7.5Hz, 2H). IR (KBr) 1482, 710 cm$^{-1}$, Anal calcd for C$_{29}$H$_{28}$BrN: C, 74.04; H, 6.00; N, 2.98. Found: C, 73.74; H, 5.92; N, 2.92.

EXAMPLE 3

N-[2'-(4,4-Dimethyl-4,5-dihydro-oxazol-2-yl)-biphenyl-4-ylmethyl]-N-propyl-N-tritylamine To a solution of the compound resulting from Example 2 (47.0 g, 0.1 mol) dissolved in anhydrous tetrahydrofuran (300 mL) at ambient temperature under nitrogen was added magnesium turnings (2.55 g, 0.105 mol). The reaction mixture was heated to reflux at which time 1,2-dibromoethane (0.43 mL) was added to initiate Grignard formation. After refluxing for 6 hours, most of the magnesium had been consumed. The reaction mixture was then allowed to cool to ambient temperature and 1-methoxy−2-(4,4-dimethyl−4,5-dihydro-oxazol-2-yl)benzene (21.54 g, 0.105 mol) was added in one portion. The reaction mixture was allowed to stir at ambient temperature overnight and then quenched by the addition of saturated aqueous ammonium chloride (300 mL) and diluted with ethyl acetate (700 mL). The organic layer was separated, washed with 5% sodium hydrogen sulfate, water, 5% aqueous sodium bicarbonate and brine, dried over magnesium sulfate and concentrated under a reduced pressure to give a yellow oil. The crude product was crystallized from methanol (200 mL) to give 44.5 g (79%) of the title compound. m.p. 151°-153° C. $^1$H NMR (CDCl$_3$, 300 MHz) δ 0.48 (t, J=7.5 Hz, 3H), 0.94-1.08 (m, 2H), 1.32 (s, 6H), 2.27 (m, 2H), 3.64 (bs, 2H), 3.79 (s, 2H), 7.18 (dd, J$_1$=J$_2$=7.2 Hz, 3H), 7.29 (dd, J=7.2Hz, 7.5Hz, 6H), 7.33-7.45 (m, 4H), 7.48 (ddd, J=7.5Hz, 7.5Hz, 1.5Hz, 1), 7.56 (d, J=7.5Hz, 2H), 7.65 (d, J=7.5Hz, 6H), 7.74 (d, J=7.2Hz, 1H). IR (KBr) 2960, 1652, 1017, 710 cm$^{-1}$ MS (DCI/NH$_3$) m/e 564 (M+H)$^+$. Anal calcd for C$_{40}$H$_{40}$N$_2$O: C, 85.06; H, 7.14; N, 4.96. Found:, C, 85.41; H, 7.09; N, 4.84.

EXAMPLE 4

N-2'-(4,4-Dimethyl-4,5-dihydro-oxazol-2-yl)-biphenyl-4-ylmethyl]-N-propylamine The compound resulting from Example 3 (21.0 g, 37.0 mmol) dissolved in methanol (16 mL), water (16 mL) and acetic acid (16 mL) was stirred at reflux for 2 hours. The reaction mixture was allowed to cool to ambient temperature and then the methanol was removed under reduced pressure. Ethyl acetate (500 mL) and 1N hydrochloric acid (50 mL) were added. The aqueous layer was separated and the organic layer extracted with 1N hydrochloric acid (10 mL). The combined aqueous extracts were washed with ethyl acetate (100 mL), basified with 2N sodium hyroxide (−45 mL) and extracted with ethyl acetate (3×200 mL). The combined organic extracts were washed with brine, dried over magnesium sulfate and concentrated under reduced pressure to give the title compound (9.42 g, 79%) as a viscous oil. $^1$H NMR (CDCl$_3$, 300 MHz) δ 0.94 (t, J=7.5Hz, 3H), 1.30 (s, 6H), 1.56 (m, 3H), 2.63 (t, J=7.5Hz, 2H), 3.80 (s, 2H), 3.84 (s, 2H), 7.31−7.42 (bm, 6H), 7.47 (m, 1H), 7.72 (bd, J=7.8Hz, 1H). IR (film) 2960, 1655, 1180 cm$^{-1}$. MS (DCI/NH$_3$) m/e 323 (M+H)$^+$.

EXAMPLE 5

Methyl 2-{N-Propyl-N-(2'-4.4-dimethyl-4,5-dihydro-oxazol-2-yl]biphenyl-4-yl)methyl]amino}pyridine-3-carboxylate The compound resulting from Example 4 (322 mg, 1 mmol), triethylamine (303 mg, 3 mmol) and methyl 2-chloronicotinate (222 mg, 1.3 mmol) were dissolved in toluene (0.5 mL) and heated at reflux for 24 hours. After cooling to 23° C., the reaction mixture was partitioned between ethyl acetate (10 mL) and saturated sodium bicarbonate (10 mL). The organic layer was dried over magnesium sulfate and concentrated in vacuo. The residue obtained was chromatographed on silica gel eluting with 1:3 ethyl acetate/hexane to give the title compound as a viscous, colorless oil (370 mg, 81%). 1H NMR (CDCl$_3$, 300 MHz) δ 0.82 (t, 3H), 1.30 (s, 6H), 1.55−1.65 (m, 2H), 3.29 (t, 2H), 3.79 (s, 2H), 3.82 (s, 3H), 4.70 (s, 2H), 6.69 (dd, 1H), 7.35−7.40 (m, 5H), 7.45−7.52 (m, 1H), 7.75 (dd, 1H), 7.91 (dd, 1H), 8.35 (dd, 1H). MS (DCI/NH$_3$) m/e 458 (M+H)$^+$.

EXAMPLE 6

Methyl 2-{N-Propyl-N-[(2'-cyanobiphenyl-4-yl)methyl]amino} pyridine-3-carboxylate yl)methyl]amino}pyridine-3-carboxylate The compound resulting from Example 5 (1.40 g, 3.06 mmol) in pyridine (10 mL) was treated with phosphorous oxychloride (0.6 mL, 6.12 mmol) and then heated at 120° C. for 4 hours. After cooled to −10° C., ethyl acetate (50 mL) was added, and the reaction mixture was washed with 1N sodium hydroxide solution (2×10 mL), water (10 mL) and brine (10 mL), dried over magnesium sulfate, concentrated in vacuo and chased with 2×10 mL of toluene to give a yellow oil. Chromatography on silica gel eluting with 1:3 ethyl acetate/hexane afforded the title compound as a viscous colorless oil (1.11 g, 94%). $^1$H NMR (CDCl$_3$, 300 MHz) δ 0.82 (s, 3H), 1.53-1.68 (m, 2H), 3.30 (t, 2H), 3.82 (s, 3H), 4.75 (s, 2H), 6.70 (dd, 1H), 7.39−7.55 (m, 5H), 7.58−7.67 (m, 1H), 7.75 (dd, 1H), 7.91 (dd, 1H), 8.28 (dd, 1H). MS (DCI/NH$_3$) m/e 386 (M+H)$^+$.

EXAMPLE 7

Methyl 2-(N-Propyl-N-(2'-1H-tetrazol-5-yl]biphenyl-4-yl)methyl]amino}pyridine-3-carboxylate A mixture of the compound resulting from Example 6 (500 mg, 1.3 mmol), trimethyltin chloride (310 mg, 1.55 mmol), sodium azide (100 mg, 1.55 mmol) in anhydrous toluene (5 mL) were heated at reflux for 36 hours. The reaction mixture was cooled to ambient temperature and ethyl acetate (20 mL) was added. This organic solution was washed with water (2×5 mL) and brine (5 mL), dried over magnesium sulfate, and concentrated in vacuo. The residue obtained was triturated with ether/hexane and dissolved in a solution of 95:5 toluene/tetrahydrofuran (5 mL) containing hydrogen chloride (130 mg, 3.6 mmol). After stirring for 2 hours, the solvent was removed under reduced pressure and the residue obtained recrystallized from ethyl acetate/hexane to give the title compound (395 mg, 71%). 1H NMR (DMSO-d$_6$, 300 MHz) δ 0.73 (t, 3H), 1.42−1.55 (m, 2H), 3.19 (t, 2H), 3.82 (s, 3H), 4.69 (a, 2H), 6.76 (dd, 1H), 7.01 (d, 2H), 7.21 (d, 2H), 7.51-7.60 (m, 2H), 7.61-7.69 (m, 2H), 7.83 (dd, 1H), 8.22 (dd, 1H). MS (DCI/NH$_3$) m/e 429 (M+H)$^+$.

EXAMPLE 8

2-{N-Propyl-N-(2'-1H-tetrazol−5-yl]biphenyl-4-yl)methyl]amino}pyridine-3-carboxylic acid The compound resulting from Example 6 (214 mg, 0.5 mmol) in 1:1 methanol/dioxane (5 mL) was treated with sodium hydroxide (100 mg, 2.5 mmol) in water (1 mL) and heated at 50° C. for 5 hours. After cooling, the reaction mixture was acidified with 12N hydrochloric acid (0.25 mL, 3 mmol). The mixture was extracted with ethyl acetate and the combined organic extracts were dried over sodium sulfate and concentrated under reduced pressure. The residue obtained was recrystallized from isopropanol to afford the title compound (183 mg, 88%). m.p. 199°−200 ° C. $^1$H NMR (DMSO-d$_6$, 300 MHz) δ 0.73 (t, 3H), 1.42−1.55 (m, 2H), 3.23 (t, 2H), 4.68 (s, 2H), 6.80 (dd, 1H), 7.01 (d, 2H), 7.22 (d, 2H), 7.51-7.59 (m, 2H), 7.61-7.71 (m, 2H), 7.88 (dd, 1H), 8.23 (dd, 1H), 13.21 (bs, 1H). MS (DCI/NH$_3$) m/e 415 (M+H)$^+$.

EXAMPLE 9

Alternate Preparation of Methyl-2-{N-Propyl-N-[(2'-[1H-tetrazol-5-yl]biphenyl-4-yl)methyl]amino}pyridine-3-carboxylate To the compound resulting from Example 6 (29 mg, 75 μmol) in enough toluene to make a 0.50 molar solution was added trimethylsilyl azide (15 μL, 110 μmol) and dibutyltin oxide (2.0 mg, 8 μmol). The reaction mixture was heated at ~105° C. for 2.25 hours. Additional trimethylsilylazide (30 μL) was added and heating was continued. After 18 hours, additional trimethylsilylazide (30 μL) was added. After 7.25 hours, an additional aliquot (30 μL) was added. After a total of 94 hours, the reaction mixture was cooled to ambient temperature, concentrated under reduced pressure and flash chromatographed on silica gel eluting with methanol in methylene chloride to afford the title compound.

EXAMPLE 10

4-Methyl-2'-1H-tetrazol-5-yl]biphenyl

To 4-methyl-2'-cyanobiphenyl (53 mg, 0.274 mmol) dissolved in toluene (0.5 mL) was added trimethylsilyl azide (100 μL, 0.73 mmol) and dibutyltin oxide (74 mg, 0.300 mmol). The reaction mixture was heated at ~105° C. for 91 hours, cooled to ambient temperature, and flash chromatographed on silica gel eluting with methanol in 1 methylene chloride to give the title compound. The 300 MHz $^1$H NMR spectrum was found to be consistent with the proposed structure.

The foregoing is merely illustrative of the invention and is not intended to limit the invention to the disclosed embodiments. Variations and changes which are obvious to one skilled in the art are intended to be within the scope and nature of the invention which are defined in the appended claims.

We claim:

1. A compound of the formula:

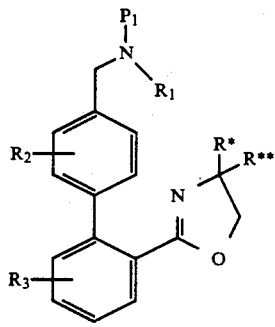

wherein $R_1$ is selected from the group consisting of hydrogen, $C_1$ to $C_7$ loweralkyl, $C_1$ to $C_7$ loweralkoxy-substituted $C_1$ to $C_7$ loweralkyl, $C_2$ to $C_{10}$ lower alkenyl, $C_2$ to $C_{10}$ lower alkynyl, $C_3$ to $C_7$ cycloalkyl and $C_3$ to $C_7$ cycloalkyl substituted $C_1$ to $C_7$ loweralkyl; $R_2$ is selected from the group consisting of hydrogen, $C_1$ to $C_7$ loweralkyl, $C_1$ to $C_7$ loweralkoxy-substituted $C_1$ to $C_7$ loweralkyl, halogen and $C_1$ to $C_7$ loweralkoxy; $R_3$ is selected from hydrogen, $C_1$ to $C_7$ loweralkyl, and halogen; $R^*$ and $R^{**}$ are independently selected from $C_1$ to $C_7$ loweralkyl and $P_1$ is hydrogen or an nitrogen-protecting group; or an acid addition salt thereof.

2. The compound of claim 1 wherein $R_2$ is hydrogen, $R_3$ is hydrogen or halogen and $R^*$ and $R^{**}$ are methyl.

3. The compound of claim 1 wherein $R_1$ is n-propyl or n-butyl, $R_2$ is hydrogen, $R_3$ is hydrogen or halogen; $R^*$ and $R^{**}$ are methyl and $P_1$ is hydrogen or trityl.

4. The compound of the formula:

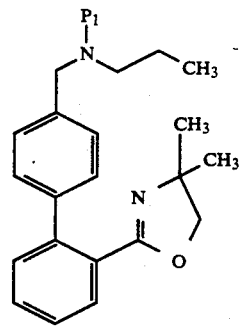

wherein $P_1$ is hydrogen or a nitrogen protecting group; and an acid addition salt thereof.

5. The compound of the formula:

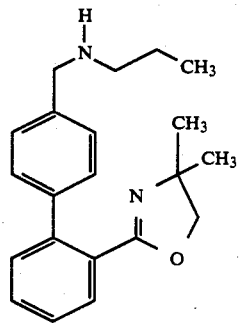

or an acid addition salt thereof.

6. The compound of the formula:

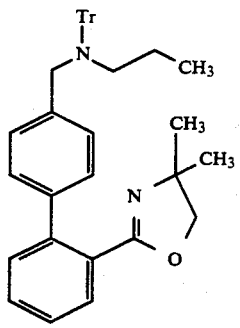

wherein Tr is trityl.

* * * * *